United States Patent [19]
Al-Chalabi

[11] 4,236,037
[45] Nov. 25, 1980

[54] PROCESS FOR THE SEPARATION OF OLEFINS

[75] Inventor: Husain A. Al-Chalabi, Des Plaines, Ill.

[73] Assignee: UOP Inc., Des Plaines, Ill.

[21] Appl. No.: 53,868

[22] Filed: Jul. 2, 1979

[51] Int. Cl.² .......................... C07C 5/23; C07C 7/00
[52] U.S. Cl. .................................. 585/670; 585/671; 585/668
[58] Field of Search .............................. 585/670, 671

[56] References Cited
U.S. PATENT DOCUMENTS

| | | | |
|---|---|---|---|
| 3,479,415 | 11/1969 | Shull | 585/664 |
| 3,752,864 | 8/1973 | Arganbright | 585/670 |
| 3,772,400 | 11/1973 | Garner | 585/670 |
| 3,793,393 | 2/1974 | Neal | 585/670 |
| 3,800,003 | 3/1974 | Sobel | 585/601 |
| 3,821,123 | 6/1974 | Germanas et al. | 585/670 |
| 3,830,870 | 8/1974 | Harter | 585/670 |
| 3,919,341 | 11/1975 | Germanas et al. | 585/670 |
| 4,104,321 | 8/1978 | Ward | 585/670 |

*Primary Examiner*—Veronica O'Keefe
*Attorney, Agent, or Firm*—James R. Hoatson, Jr.; John G. Cutts, Jr.; William H. Page II

[57] ABSTRACT

A butene mixture is separated to yield a n-butene rich product and an isobutylane rich product in a fractionator system. Other suitable olefins may be separated in a similar manner.

6 Claims, 1 Drawing Figure

U.S. Patent     Nov. 25, 1980     4,236,037
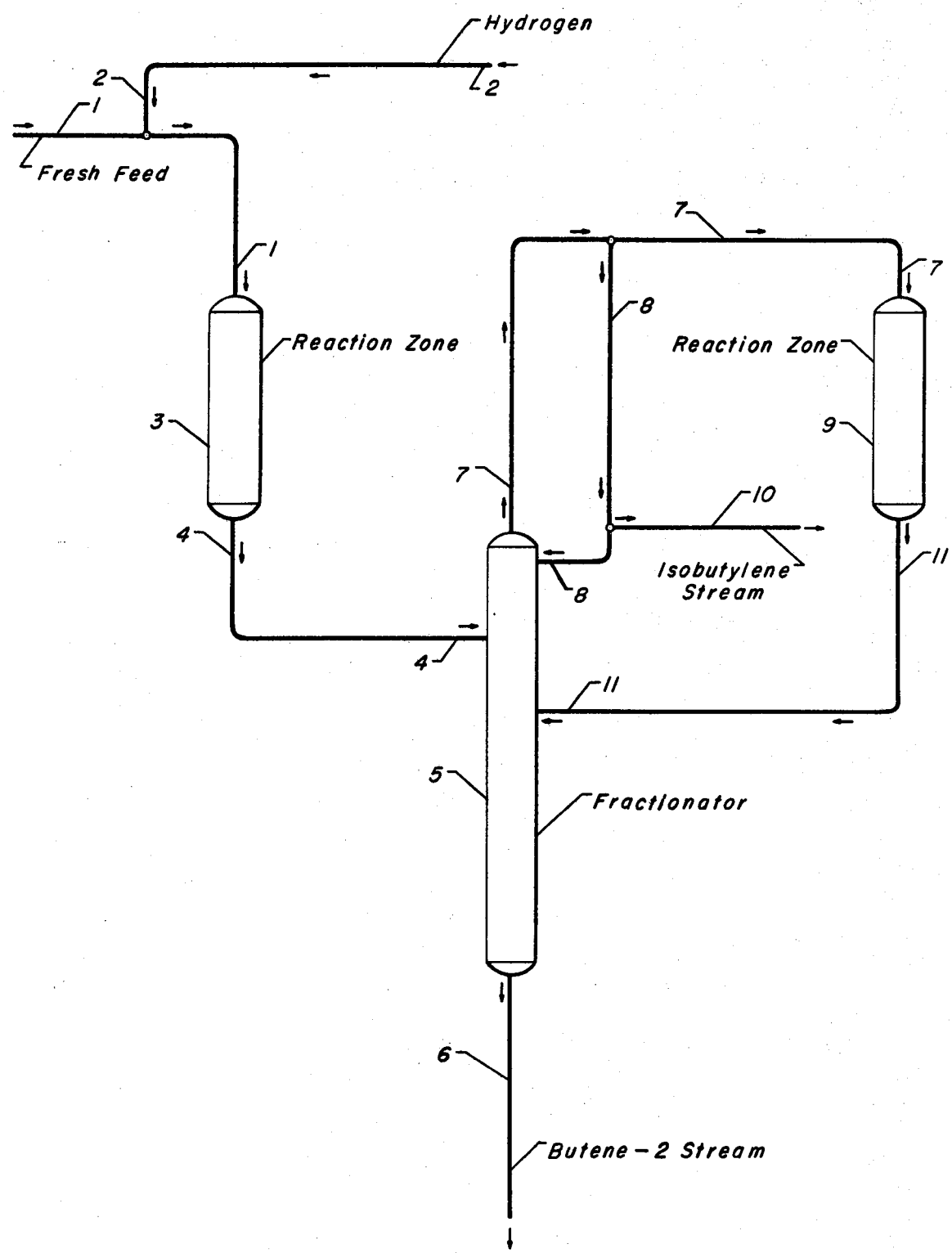

PROCESS FOR THE SEPARATION OF OLEFINS

BACKGROUND OF THE INVENTION

This invention relates to a process for the separation of a butene mixture to produce a n-butene rich product and an isobutylene rich product in a fractionator wherein a portion of the fractionator overhead is isomerized and the entire isomerization effluent is introduced into the fractionator at a locus below the locus of the reflux. The resulting high purity streams and isobutenes are useful in subsequent reactions to produce secondary butyl alcohol and methyl ethyl ketone from normal butylene and butyl rubber and lubricating oil additive from isobutylene.

The isomerization of olefins is generally well known in the petroleum refining art. The double bonds present in olefinic hydrocarbons shift readily over various catalysts to a more central position in the organic molecule. Compositions of a metal from Group VIII of the Periodic Table, properly inhibited in their hydrogenation activity, with a refractory inorganic oxide are well known catalysts in producing olefinic bond migration.

SUMMARY OF THE INVENTION

It is an object of this invention to provide an economical method for isomerizing, and separating butene isomers via a novel fractionation and reaction process. In a broad embodiment, the present invention relates to a process for separating iso-olefins and normal olefins from a mixture thereof which comprises the steps of: (a) subjecting said mixture to isomerization in a first isomerization zone to convert a portion of the normal olefin hydrocarbon to iso-olefin; (b) fractionating the resultant isomerization zone effluent in a fractionation zone to separate the same into an iso-olefin-rich stream containing normal olefin and a normal olefin-rich stream of reduced iso-olefin content; (c) subjecting at least a portion of said iso-olefin-rich stream to isomerization in a second isomerization zone to isomerize normal olefin hydrocarbons contained therein; (d) refluxing at least a portion of said iso-olefin-rich stream derived from the aforesaid fractionating step (b); (e) recovering an iso-olefin product derived from the aforesaid fractionating step (b); (f) returning essentially the entire effluent from said second isomerization zone derived from the aforesaid step (c) to said fractionation zone at a locus below the reflux locus.

Another embodiment of the present invention relates to a process for producing isobutylene from a mixture containing normal butenes and isobutylene which comprises the steps of: (a) subjecting said mixture to isomerization in a first isomerization zone to convert a portion of the normal butenes to isobutylene; (b) fractionating the resultant isomerization zone effluent in a fractionation zone to separate the same into an isobutylene-rich stream containing normal butenes and a normal butene-rich stream of reduced isobutylene content; (c) subjecting at least a portion of said isobutylene-rich stream to isomerization in a second isomerization zone to isomerize normal butene hydrocarbons contained therein; (d) refluxing at least a portion of said isobutylene-rich stream derived from the aforesaid fractionating step (b); (e) recovering an isobutylene product derived from the aforesaid fractionating step (b); and (f) returning essentially the entire effluent from said second isomerization zone derived from the aforesaid step (c) to said fractionation zone at a locus below the reflux locus.

The normal boiling point of 1-butene is about 20° F. and the normal boiling point of isobutylene is about 19.6° F. These boiling points are quite close together, so that separating 1-butene from isobutylene by conventional fractionation is impractical. The normal boiling points of cis- and trans-2-butene are about 38.7° F. and 33.6° F., respectively, so that isobutylene and 1-butene can be separated from 2-butene by fractionation. Such a separation, however, is not capable of providing a high purity isobutylene stream, substantially free from 1-butene. By employing the method herein disclosed, 1-butene can be significantly reduced from an isobutylene product stream. Therefore, a high purity isobutylene product stream may be provided from a conventional source of butene isomer mixture.

Further objects, embodiments and illustrations indicative of the broad scope of the present invention will be apparent to those skilled in the art from the description of the drawing and preferred embodiments of the invention hereinafter provided.

DESCRIPTION OF THE DRAWING

The attached drawing is a schematic flow diagram and illustrates a particular embodiment of the present invention. Referring to the drawing, a conventional butylene feed, comprising 44 weight percent 1-butene, 44 weight percent isobutylene and 12 weight percent 2-butene, is charged through conduit 1 and hydrogen is charged through conduit 2. The combined butylene feed and hydrogen is passed via conduit 1 into reaction zone 3 which is maintained at olefin isomerization conditions. The hydrocarbons charged to reaction zone 3 are contacted with a fixed bed of an isomerization catalyst comprising nickel and sulfur on a porous carrier. The catalyst is prepared by forming an initial composite of nickel-carrier material, sulfiding and then stripping sulfur from the catalyst with hydrogen to provide a final isomerization catalyst. This catalyst is hereafter being called a nickel subsulfide catalyst. The hydrocarbons are passed continuously through reaction zone 3 at a liquid hourly space velocity (volume of charge per volume of catalyst per hour) of about 0.1 to about 20, preferably in downward flow over the catalyst bed, and continuously withdrawn from reaction zone 3 through conduit 4. The isomerization reactor effluent in conduit 4 is charged to fractionator 5, which is a conventional fractionation vessel. The isomerization reactor effluent has a reduced level of 1-butene with an essentially corresponding increased level of cis-2-butene and trans-2-butene. Because of a thermodynamic equilibrium constraint, the 1-butene level will be at least five to fifteen percent of the normal butene fraction. In fractionator 5, a mixture of isobutylene and 1-butene is separated and withdrawn overhead through conduit 7. A portion of the mixture of hydrocarbons in conduit 7 passes to conduit 8 and is returned to fractionator 5 as reflux. A slipstream from conduit 8 is withdrawn via conduit 10 as an isobutylene product stream. The remaining portion of hydrocarbon in conduit 7 passes to reaction zone 9 which is maintained at olefin isomerization conditions. The hydrocarbons charged to reaction zone 9 are contacted with a fixed bed of an isomerization catalyst comprising a nickel subsulfide catalytic material. The resulting isomerized hydrocarbon is withdrawn from reaction zone 9 via conduit 11 and is introduced into fractionator 5 at a locus which is lower than the locus of the reflux. Various conventional equipment and operations have not been described in the foregoing, such as pumps, valves, heat exchange means, etc. The use of such conventional equipment and operations will be understood to be essential and the method of their use in the process of the present invention will be obvious to those skilled in the art.

DETAILED DESCRIPTION OF THE INVENTION

The olefinic feedstock containing 1-butene, 2-butene and isobutylene employed in the present process may comprise solely butene isomers, or may contain other hydrocarbons. It is contemplated that the olefinic feed employed normally comprises a mixture of 1-butene, 2-butene and isobutylene. However, other materials may be present in the olefin feedstock, including for example, paraffins, naphthenes or aromatics, as well as minor amounts of contaminants. A suitable olefinic feedstock may contain some propane, normal butene, isobutane, pentane, butadiene, etc., which hydrocarbons are often present in minor amounts in a conventional olefinic feedstock source. It is preferred, however, that the olefinic feedstock employed in the present process contain at least about 50 weight percent $C_4$ olefins. The olefinic feedstock in the process of the present invention is first contacted with an isomerization catalyst in an isomerization reaction zone at olefin isomerization conditions. Isomerization catalysts which can be employed in the isomerization operation of the present invention include catalysts which produce a shift of the olefinic bond in 1-butene to a more central position in the hydrocarbon molecules to form 2-butene. Various catalysts have been found suitable in the prior art, including, for example, alumina, silica, zirconia, chromium oxide, boron oxide, thoria, magnesia, aluminum sulfate and combinations of two or more of the foregoing.

Also employed have been acidic catalysts such as sulfuric acid, phosphoric acid, aluminum chloride, etc., either in solution or on a solid support. Also suitable for use in the isomerization operation as an isomerization catalyst is a sulfided nickel on a porous carrier material such as described in U.S. Pat. No. 3,821,123. Thermal isomerization may be utilized, but suffers from the defects of producing excessive amounts of side products.

The preferred method by which the operation of the isomerization step of the present process may be effected is a continuous-type operation. One particular method is a fixed bed operation in which the feedstream comprising butene isomers is continuously charged to an isomerization reaction zone containing a fixed bed of catalyst, the reaction zone being maintained at olefin isomerization conditions including a temperature in the range from about 0° to about 400° F. or more, and a pressure of about 1 atmosphere to about 200 atmospheres or more. A preferred temperature is about 80° to about 300° F. and a preferred pressure is about 4 atmospheres to about 50 atmospheres. The charge of butene isomers is passed over the catalyst bed in either an upward or downward flow and withdrawn continuously and recovered. It is contemplated within the scope of the present invention that gases such as hydrogen, nitrogen, etc., may be continuously charged to the isomerization zone as desired.

Another continuous-type operation comprises a moving bed-type in which the butene isomers feed and the catalyst bed move co-currently or counter-currently to each other while passing through the isomerization zone.

Conventional sources of $C_4$ olefins contain a mixture of 1-butene, 2-butene and isobutylene. Although various attempts have been made in the prior art to isomerize 1-butene by shifting the olefinic bond to provide 2-butene, it has been found, in general, that olefin isomerization conditions which favor economically desirable high conversion of 1-butene also tend to favor polymerization of isobutylene, a highly undesirable side reaction. The prior art has thus been limited to lower than optimum conditions of 1-butene conversion to 2-butene when isobutylene is present in the feed stream. The process of the present invention at least partially overcomes the problems thereby created. In the present process, it is not necessary to maintain olefin isomerization conditions such that an extremely high conversion of 1-butene is achieved, so that polymerization of isobutylene is thereby avoided, at the same time, by changing at least a portion of the fractionator overhead vapors containing 1-butene and isobutylene directly to an isomerization reaction zone and then introducing the isomerized effluent to the fractionator at a locus below the locus of the reflux, the concentration of 1-butene in the net overhead isobutylene product stream is significantly reduced. The introduction of the isomerized fractionator overhead at a locus below the reflux locus permits additional fractionation of the isomerized overhead before the eventual removal of these hydrocarbons in the product streams. The selection of an appropriate locus for the introduction of the isomerized fractionator overhead may be dictated by the desire to have the concentration of the hydrocarbon species present in such an isomerized stream closely match the concentration of similar hydrocarbon species which are present in the rising vapor phase within the fractionator at the selected locus. Other criteria which may be used to locate the appropriate locus for the introduction of the isomerized fractionator overhead are minimization of fractionator size, minimization of utility cost or any other engineering optimization scheme. Also at the same time, by refluxing at least a portion of the fractionator overhead, the concentration of 1-butene in the net overhead isobutylene product stream is significantly reduced. Other suitable olefins may be selected from pentenes, hexenes, etc.

The process of the present invention is further illustrated by the following examples. These examples are, however, not present to unduly limit the process of this invention, but to further illustrate the hereinabove embodiments.

EXAMPLE I

A standard, conventional distillation column is charged with 10,000 mols per day of a mixed butene stream having the characteristics displayed in Table I.

TABLE I

|  | Feed | Overhead Product | Bottoms Product |
|---|---|---|---|
| 1-butene, mols | 650 | 588 | 62 |
| Isobutylene, mols | 3500 | 3250 | 250 |
| Cis-2-butene, mols | 2925 | 6 | 2919 |
| Trans-2-butene, mols | 2925 | 36 | 2889 |
|  | 10000 | 3880 | 6120 |

The distillation column contains at least 80 theoretical stages and is refluxed at about 80,000 mols/day. Inspections of the overhead and bottoms products are shown in Table I and indicate that the isobutylene overhead stream has a purity of 84% and that the 2-butene bottoms stream has a purity of 95%.

EXAMPLE II

The identical distillation column used in Example I is modified by incorporating an olefin isomerization reaction zone in the column's overhead line after a slipstream has been removed to provide a reflux stream and a net product stream. The reaction zone effluent is returned to the fractionator at a locus defined by the seventh fractionation tray below the locus of the reflux. The locus of the reflux is the top fractionation tray of the fractionator and the reflux volume is about 40,000 mols/day. The feed to the above-described column as modified is charged with 10,000 mols per day of a mixed butene stream having the same characteristics as the Example I feed and displayed in Table II.

TABLE II

|  | Feed | Overhead Product | Bottoms Product |
|---|---|---|---|
| 1-butene, mols | 650 | 59 | 6 |
| Isobutylene, mols | 3500 | 3250 | 250 |
| Cis-2-butene, mols | 2925 | 7 | 3178 |
| Trans-2-butene, mols | 2925 | 42 | 3208 |

Inspection of the overhead and bottoms products are shown in Table II and indicate that the isobutylene overhead stream has a purity of 96.8% and that the 2-butene bottoms stream has a purity of 96.9%.

From the foregoing examples, the beneficial import of the process of this invention is readily ascertainable by those skilled in the art.

I claim as my invention:

1. A process for the separation of iso-olefin and normal olefin hydrocarbons from a mixture containing the same, which comprises the steps of:
   (a) subjecting said mixture to isomerization in a first isomerization zone to convert a portion of the normal olefin hydrocarbon to iso-olefin;
   (b) fractionating the resultant isomerization zone effluent in a fractionation zone to separate the same into an iso-olefin-rich stream containing normal olefin and a normal olefin-rich stream of reduced iso-olefin content;
   (c) subjecting at least a portion of said iso-olefin-rich stream to isomerization in a second isomerization zone to isomerize normal olefin hydrocarbons contained therein;
   (d) refluxing at least a portion of said iso-olefin-rich stream derived from the aforesaid fractionating step (b);
   (e) recovering an iso-olefin product derived from the aforesaid fractionating step (b);
   (f) returning essentially the entire effluent from said second isomerization zone derived from the aforesaid step (c) to said fractionation zone at a locus below the reflux locus.

2. The process of claim 1 wherein said olefins are butenes.

3. The process of claim 1 wherein said olefins are pentenes.

4. The process of claim 1 wherein said olefins are hexenes.

5. The process of claim 1 wherein said isomerization is catalyzed by a refractory inorganic oxide selected from alumina, silica, zirconia, chromium oxide and magnesia.

6. The process of claim 1 wherein said isomerization is catalyzed by a partially sulfided nickel catalyst.

* * * * *